United States Patent
Oberley

[11] 3,957,494
[45] May 18, 1976

[54] CHROMATED COPPER ARSENATE WOOD PRESERVATIVE COMPOSITIONS

[75] Inventor: William J. Oberley, Monroeville, Pa.

[73] Assignee: Koppers Company, Inc., Pittsburgh, Pa.

[22] Filed: Sept. 30, 1974

[21] Appl. No.: 510,493

[52] U.S. Cl. ............................ 106/15 R; 424/137; 424/140; 427/440
[51] Int. Cl.² .......................................... C09D 5/14
[58] Field of Search .............. 106/15 AF; 424/137, 424/140; 117/151; 427/440; 148/6.2

[56] References Cited
UNITED STATES PATENTS

| | | | |
|---|---|---|---|
| 2,041,655 | 5/1936 | Gunn | 117/151 |
| 2,230,748 | 2/1941 | Hager | 117/151 |
| 3,080,212 | 3/1963 | Oberley et al. | 424/137 |
| 3,266,985 | 8/1966 | Swales | 424/140 |
| 3,523,049 | 8/1970 | Putman | 106/15 AF |

Primary Examiner—Lorenzo B. Hayes
Attorney, Agent, or Firm—Herbert J. Zeh, Jr.; Oscar B. Brumback

[57] ABSTRACT

Chromated copper arsentate wood preserving solutions in which the ratio of hexavalent chromium to trivalent chromium in the solution is between about 4.0:1.0 to about 1.0:1.0 give improved penetration into the wood, better retention of preservative in the wood, and improved stability of the treating solution. The solutions contain an acid to maintain the required pH, prevent corrosion, and further improve the solution stability.

4 Claims, No Drawings

CHROMATED COPPER ARSENATE WOOD PRESERVATIVE COMPOSITIONS

BACKGROUND OF THE INVENTION

This invention relates to improved chromated copper arsenate wood treating compositions. More particularly, this invention is directed to chromated copper arsenate wood treating solutions in which the ratio of hexavalent chromium (Cr+6) to trivalent chromium (Cr+3) is between about 4.0:1.0 to about 1.0:1.0. The chromated copper arsenate solutions having ratios of Cr+6 to Cr+3 within this range provide improved penetration into the wood, better retention of preservative in the wood, and improved stability of the treating solutions. The solutions also contain an acid. The acid is selected to maintain the desired pH while further improving solution stability and preventing corrosion. This invention also relates to the treatment of wood with the improved compositions to prevent decay, fungi, rot, termites and the like.

During recent years the group of wood preservatives known as chromated copper arsenates (CCA) have become of great importance. These CCA compositions are one of the most widely used type of wood preserving compounds in use today. These preservatives contain as active ingredients copper as cupric ion, chromium usually as the dichromate ion and arsenic as acid arsenate ion. In addition, the CCA compositions may also contain inert ions and salts such as sodium ion, sulfate ion, and/or sodium sulfate. These inert ions and salts are the side products which are formed when the CCA compositions are formulated from the least expensive source of active ingredients usually available; for example, copper sulfate as the copper source and sodium dichromate as the chromium source. Generally the compositions contain from about 40.0 to about 70.0% by weight chromium measured as $CrO_3$, from about 15 to about 23% by weight copper measured as CuO, and from about 14 to about 50% by weight arsenic measured $As_2O_5$.

Typical formulations of some of the widely used CCA compositions of the prior art are as follows: Greensalt which is 56% $Na_2Cr_2O_7 \cdot 2H_2O$ or $K_2Cr_2O_7$, 33% $CuSO_4 \cdot 5H_2O$, 11% $AS_2O_5 \cdot 2H_2O$; Tanalith C which is 45% $Na_2Cr_2O_7 \cdot 2H_2O$ or $K_2Cr_2O_7$, 35% $CuSO_4 \cdot 5H_2O$, 20% $As_2O_5 \cdot 2H_2O$; and Celcure A which is 40% $Na_2Cr_2O_7 \cdot 2H_2O$ or $K_2Cr_2O_7$, 32% $CuSO_4 \cdot 5H_2O$, 28% $As_2O_5 \cdot 2H_2O$. In recent years, the American Wood Preservers Association (AWPA) has standardized the formulations of CCA compositions. The formulations have been converted for greater ease in specification into a uniform nomenclature based on the oxides $CrO_3$, CuO and $As_2O_5$. The currently adapted standardized American formulations have the following compositions in percent by weight:

|  | CCA-Type A | CCA-Type B | CCA-Type C |
| --- | --- | --- | --- |
| $CrO_3\%$ | 65.5 | 35.3 | 47.5 |
| CuO% | 18.1 | 19.6 | 18.5 |
| $As_2O_5\%$ | 16.4 | 45.1 | 34.0 |

The formulations are prepared and sold as concentrated solutions containing from about 45 to 75% active oxides in water. The concentrated solutions are then diluted to about 1 to 10% active oxides for use in treating wood.

Several patents have issued on the use of chromated copper arsenate wood preservative compositions. See for example, Hager, U.S. Pat. No. 2,202,579; 2,366,612; 2,432,007, and 2,565,175. In addition see McMahon, U.S. Pat. No. 2,438,511, Kamesam, U.S. Pat. No. 2,106,978, Oberley et al, U.S. Pat. No. 3,080,212, Henriksson et al, U.S. Pat. No. 3,793,441 and Nicholson, U.S. Pat. No. 3,832,463. All of these patents disclose the use of chromated copper arsenate compositions which are useful in preserving wood. However, all of the compositions contain the chromium only in the hexavalent state.

Chromated copper arsenate solutions are particularly effective preservatives for the prevention of decay and deterioration of wood,. Wood impregnated with chromated copper arsenate solutions are resistant to decay and attack by termites and at the same time the active ingredients are resistant to weathering and leaching when wood treated with the compositions is in contact with the ground or water. Moreover, the treated wood does not bloom and hence the surface of the treated wood may be painted.

Heretofore, wood was commonly treated with chromated copper arsenate solutions in which the chromium was present in the hexavalent form. Treatment with these prior art chromated copper arsenate solutions had several drawbacks. First, there is incomplete penetration of the chromated copper arsenate solutions into the wood. This is particularly true of refractory species of wood such as Douglas fir. In addition, the initial retention of the chromated copper arsenate compositions is not as high as is desirable. Another drawback of the prior art CCA treating solutions is their instability in the presence of reducing sugars normally found in most untreated woods. The CCA solutions react with the reducing sugars during treatment to form sludgy precipitates. The precipitates interfere with penetration and retention, greatly reduces the usable life of the treating solution and causes corrosion of the treating equipment. This results in a large chemical and monetary loss.

It is, therefore, the object of this invention to provide an improved chromated copper arsenate wood treating solution which overcomes the drawbacks of the prior art chromated copper arsenate solutions by providing improved penetration, retention, and solution stability.

SUMMARY OF THE INVENTION

It has been found in accordance with this invention that chromated copper arsenate wood treating solutions having a ratio of hexavalent chromium to trivalent chromium between about 4.0:1.0 and about 1.0:1.0 give improved penetration, improved retention and improved solution stability. The preferred solutions have a ratio of hexavalent chromium to trivalent chromium of about 2.2:1.0 to about 1.5:1.0. The solution also contains an acid to maintain the desired acidic pH, improve solution stability, and help prevent corrosion of the treating equipment. When wood is treated with the solutions of this invention, the results are improved penetration of the solution into the wood and improved retention of the CCA in the wood. In addition, the formation of harmful precipitates during impregnation is avoided, as well as other drawbacks such as corrosion of the treating equipment.

The improved chromated copper arsenate wood treating compositions of this invention are essentially the same as the commercially used compositions, except that the chromium is present in a controlled ratio of $Cr+6$ to $Cr+3$ of from about 4.0:1.0, to 1.0:1.0, preferably 2.2:1.0 to 1.5:1.0. The compositions consist essentially of from about 40.0% to about 70.0% by weight chromium measured as $CrO_3$, from about 15% to about 23% copper measured as $CuO$ and from about 14% to about 50% by weight arsenic measured as $As_2O_5$, and have a ratio of hexavalent chromium to trivalent chromium of from about 4:1 to 1:1. The improved CCA solutions are preferably the same as the currently adopted standardized American formulations shown above with the modification that the chromium exists in a controlled ratio of hexavalent chromium to trivalent chromium.

The chromated copper arsenate compositions of this invention may be prepared by reducing part of the chromium in a standard formulation so that the resulting composition has the required ratio of hexavalent chromium to trivalent chromium. The chromium in the standard CCA solutions can be reduced by a variety of reducing agents in either a concentrated or dilute system. Alternatively the CCA compositions of this invention may be prepared by using starting materials that will yield standard CCA solutions having the desired ratio of plus 6 to plus 3 chromium. Economics will dictate to a large extent the method ultimately used commercially, For example, chromated copper arsenate compositions within the scope of this invention have been prepared from $CrO_3$, $Cr_2(SO_4)_3$, $As_2O_5$, and $CuSO_4$. The hexavalent chromium was supplied from the $CrO_3$ and the trivalent chromium from the $Cr_2(SO_4)_3$. The ratio of hexavalent to trivalent may be controlled by varying the amounts of $Cr_2(SO_4)_3$ and $CrO_3$ employed.

Many different reducing agents have been used to modify the heretofore standard CCA solutions to CCA solutions which fall within the scope of this invention. For example, such reducing agents as methanol, phosphorous acid, sulfur dioxide, sulfurous acid, and hydrogen peroxide have been used. When choosing the reducing agent, it must be remembered that chromium complexes with a variety of organic ligands and care must be used in order to prevent the formation of such complexes. One such reducing agent that forms a complex is formic acid. The use of formic acid alone would not be desirable and if formic acid is to be used an additional compound such as palladium or platinum should be employed to break up the undesirable complex.

The improved CCA solutions of this invention may have concentrations varying from about 1% by weight active ingredients to about 75% by weight active ingredients. Solutions prepared for shipment to treating plants will generally have concentrations of 45 to 75%, usually around 50%, by weight active oxides. Solutions used for actually treating the wood will generally have concentrations of from 1 to 10% by weight preferably from 1 to 5 percent. Solutions containing less than 1% chromated copper arsenate are generally not as effective as necessary while solutions greater than 10% are generally not needed for effective treatment and hence are wasteful and may create treatment problems.

As mentioned above, it is necessary to add an acid to the CCA solutions of this invention. The acid should be added in sufficient quantities to lower the pH of the solution to below a pH of about 2. The use of a reducing agent tends to raise the pH of the solution above a pH of about 2 which causes insoluble chromated copper arsenates to precipitate out of solution before the wood is treated. Therefore, it is necessary to add sufficient acid to maintain the pH below about 2 until the wood is impregnated and the reaction in the wood raises the pH above 2 and precipitates out the insoluble chromated copper arsenate preservative in the wood. The use of an acid also adds another beneficial effect. By properly choosing the acid the corrosion problem attendant with treating wood with chromated copper arsenates may be prevented or avoided.

It is a critical feature of this invention that the ratio of hexavalent chromium to trivalent chromium must be within the range of from about 4.0:1.0 to 1.0:1.0. If the ratio is not within this range, the improved penetration, retention, and solution stability of this invention will not be obtained. In addition, if the concentration of hexavalent chromium is too low with respect to the trivalent chromium, there will be insufficient hexavalent chromium to react with the wood and raise the pH sufficiently to form insoluble precipitates of chromated copper arsenate. It is also known that if the concentration of trivalent chromium becomes too high, copper will be plated out of solution under acidic solutions. As mentioned above it is also a requirement of this invention to adjust the pH of the treating solution below a value of about 2.0, preferably about 1.7. If the pH of the solution is not below about 2.0 premature precipitation of the preservative occurs. In adjusting the pH care should be used so the pH is not so low that the amount of hexavalent chromium in the treating solution is insufficient to react in the wood and raise the pH above about 2.2 to cause precipitation in the wood of insoluble chromated copper arsenate. In addition very acidic solutions may destroy the wood. The practical minimum pH is about 1.5.

The aqueous modified CCA solutions of this invention having the required ratio of $Cr+6$ to $Cr+3$ are excellent wood preservative compositions, especially for refractory species such as Douglas fir. The wood may be treated with the improved CCA solutions by one of the various techniques which are well known in the art. Examples of some of these methods are soaking, diffusion into green wood, full cell and empty cell pressure impregnation, compression impregnation, and the like. The particular technique used will be determined by such factors as the species of wood being treated, the thickness and shape of the wood, the degree of treatment required, and other factors readily known to one in the art.

The most commonly used technique for treating wood with CCA solutions is pressure impregnation. The pressure employed will depend on the species and thickness of wood. Some kinds of wood require only minimal pressure whereas others require much greater pressures. Care must be taken so that the pressure is not so great as to degrade the wood. Useful wood impregnation pressures generally range between about 25 and 200 psi. The pressures may be varied to permit the use of either the full cell or the empty cell process. The time required for complete penetration varies with the species of wood, thickness of wood, and pressure. Generally 4 to 12 hours produce satisfactory results.

Numerous experiments have been performed demonstrating the effectiveness of this invention. The following examples illustrate the invention, but should not be construed to limit the same.

Example 1

An improved chromated copper arsenate solution having a ratio of hexavalent to trivalent chromium within the scope of this invention was prepared as follows. A standard CCA type C fomulation was prepared by dissolving 23.75 gms of $CrO_3$, 9.25 gms of CuO, and 17.0 gms of $As_2O_5$ in 50 gm of water to give 100 gms of a 50% active CCA-C solution. Then 22 gms of 85% $H_3PO_4$ and 8.0 gms 96% $H_2SO_4$ were added to the CCA solution. Then 13.5 gms of 31.4% $H_2O_2$ were added to 56.5 gms water and this dilute solution of hydrogen peroxide was slowly added to the CCA solution and the reduction reaction proceeded very vigorously. The result was a solution containing 25% by weight active chromated copper arsenate having a ratio of hexavalent chromium to trivalent chromium of 65/35. The solution also contained acids selected to maintain the desired pH and prevent corrosion.

Example 2

An improved chromated copper arsenate solution having a ratio of hexavalent to trivalent chromium within the scope of this invention was prepared as follows. A standard CCA-Type C formulation was prepared by dissolving 23.75 gms of $CrO_3$, 9.25 gm CuO, and 17.0 gms $As_2O_5$ in 50 gms water to give 100 gms of a 50% active CCA-C solution. Then 1.33 gms of methanol and 28.67 gms of water were mixed and the dilute aqueous methanol solution was slowly added to the CCA solution. The reaction proceeded vigorously with a noticeable exotherm. The result was a solution containing 25% by weight active chromated copper arsenate having a ratio of hexavalent chromium to trivalent chromium of 65/35.

Example 3

An improved chromated copper arsenate solution having a ratio of hexavalent to trivalent chromium within the scope of this invention was prepared as follows. First 200 gms of a 50% active CCA-Type C solution was prepared in a manner similar to that described in Example 1. Then 12.85 gms $H_2SO_3$ and 7.6 gms $H_3PO_3$ were dissolved in 100 gms of water and added to the CCA solution. Finally 33.3 gms of 85% $H_3PO_4$ and 46.25 gms of water were added to the solution. The result was a solution containing 25% by weight active chromated copper arsenate having a ratio of hexavalent chromium to trivalent chromium of 65/35.

Example 4

An improved chromated copper arsenate solution having a ratio of hexavalent to trivalent chromium within the scope of this invention was prepared as follows. First 47.5 gms $CrO_3$ and 10.9 gms of 70.3% $H_3AsO_4$ were dissolved in 68.9 gms of water. Then 24.3 gms $As_2O_3$ were slowly added and the reaction temperature maintained near the boiling point. Then the solution was cooled to room temperature and 21.6 gms of 85% $H_3PO_4$, 8.6 gms 96% $H_2SO_4$ and 26.4 gms of $CuCO_3$ were added. Finally sufficient water was added to dilute the concentration of chromated copper arsenate to 25% by weight. The chromated copper arsenate solution had a ratio of hexavalent chromium to trivalent chromium within the range of this invention. The $H_3PO_4$ is a sludge inhibitor, corrosion inhibitor, and buffer, and the $H_2SO_4$ adjusts the final pH of the solution below 2 ($\approx$ 1.7). During the reduction part of the haxavalent chromium was converted to trivalent chromium and at the same time the arsenic was oxidized to the pentavalent form.

Example 5

A modified CCA-type C wood treating solution was prepared by dissolving 17.0 lbs. of a 50% CCA-C solution in 212.5 lbs. of water. Then 3.68 lbs. 85% $H_3PO_4$ and 1.47 lbs. of 96% $H_2SO_4$ were added. Then 2.41 lbs. of a 30% solution of hydrogen proxide was dissolved in 85.0 lbs. of water. The dilute hydrogen peroxide was slowly added to the CCA solution. Then the modified CCA solution was adjusted to 4% by the addition of 103.2 lbs. water. A standard 4% CCA-C solution was also prepared. Wood was impregnated with the standard CCA solution and the improved CCA solution of this invention. The wood selected for the study was construction grade Douglas fir heartwood and 20 pieces of $2 \times 4 \times 10$ feet were used. Each 10 feet piece was cut into two 5 feet pieces which were labeled A and B. The A series of samples were treated with the CCA solution of this invention. The B series of samples were treated with the standard CCA solution. The full cell treating cycle was used for both sets of samples. The cycle was as follows: (a) Initial vacuum for 1 hour at 26 inches Hg and (b) Pressure for 8 hours at 125 psig. The retentions of the samples were determined by weighing the wood before and after treatment. The results showed that the average retentions for the 20 pieces treated with the modified CCA solutions of this invention was 18.5 lbs. per cubic foot (pcf) and the average retention for the 20 pieces treated with the CCA standard solution was 11.7 pcf. This clearly demonstrates that the CCA solutions of the present invention provide greater than a 50% increase in retention in hard to treat wood. The penetration of treating solutions into the samples was determined by applying an arsenic stain to the ends of all the samples after 1 foot was cut from each end of each sample (AWPA A-3). The results showed a much greater penetration (severalfold increase) with the CCA solutions of this invention compared to the CCA standard solutions.

Example 6

An improved chromated copper arsenate solution have a ratio of hexavalent to trivalent chromium within the scope of this invention was prepared as follows. First, 100 gms of a 50% active CCA-Type C solution was prepared in a manner similar to Example 1. Then 62 gm water, 4gm $H_2SO_4$, and 4gm $HNO_3$ were added. Then 1.21 gm methanol was dissolved in 28.79 gm. water and the dilute methanol was slowly added to the CCA solution. The resulting solution was heated to 45°C for about 3 hours. The result was a 25% active solution having a ratio of hexavalent chromium to trivalent chromium of about 65/35. A 2% active solution was prepared by diluting the 25% active solution with water. This solution was used to treat wood and gave improved penetration and retention.

Example 7

An improved chromated copper arsenate treating solution having a desired ratio of hexavalent to trivalent chromium of about 65/35 was prepared as follows. First 105.2 gms of $Cr_2(SO_4)_3$, 93.0 gms $CuSO_4$, 105.0 gms of 70% $H_3AsO_4$ and 19.0 gms $CuO_3$ were dissolved in 7,658.8 gms. of water. The result is a wood treating solution containing 2% active chromated copper arsenate having the desired ratio of Cr+6 to Cr+3. A standard CCA-C solution was also prepared and diluted to 2% active. In order to produce some of the difficulties normally associated with reusing the treating solutions, 18 end grain wafers of about ⅛ inch thickness cut from Douglas fir 2 ×4's were placed in each of the above CCA solutions. The solutions were periodically agitated for a 24-hour period. The two 2% CCA wood treating solutions were then used to treat 1 foot long sections of Douglas fir 2× 4's which were refractory in nature. The treatment was Full Cell using ½ hour vacuums of 26 inches Hg followed by 4 hours pressure of 150 psig. at room temperatures. The retention of the modified CCA was 21.0 pcf while the retention of the standard CCA solution was 12.9 pcf. The two treating solutions containing the wood wafers were kept at room temperatures with periodic agitation for three weeks. After 3 weeks the pH of the solutions were measured. The pH of the modified CCA solutions of this invention was 1.65 while the pH of the standard CCA solution was 2.45. The stability and usefulness of the solutions are detrimentally affected when the pH is above 2.0.

Example 8

A series of 2% chromated copper arsenate solutions having various ratios of hexavalent chromium to trivalent chromium were prepared by dissolving the ingredients in water. The following formulations were prepared:

| Formulation Number | Ratio of Cr+6/Cr+3 | $CrO_3$ | $Cr_2(SO_4)_3$ | $CuSO_4$ | 70% $H_3A_5O_4$ | $H_2O$ |
|---|---|---|---|---|---|---|
| 1 | 50/50 | 4.75 | 12.11 | 11.63 | 13.07 | 958.44 |
| 2 | 55/45 | 5.23 | 10.88 | 11.63 | 13.07 | 959.19 |
| 3 | 60/40 | 5.69 | 9.71 | 11.63 | 13.07 | 959.90 |
| 4 | 65/35 | 6.17 | 8.48 | 11.63 | 13.07 | 960.65 |
| 5 | 70/30 | 6.65 | 7.26 | 11.63 | 13.07 | 961.39 |
| 6 | 75/25 | 7.11 | 6.09 | 11.63 | 13.07 | 962.10 |

These solutions are useful in treating wood, particularly refractory species, and give improved penetration and retention.

I claim:

1. In a chromated copper arsenate wood treating solution of the type comprising as active ingredients from about 40.0 to about 70.0 % by weight chromium measured as $CrO_3$, from about 15 to about 23 % by weight copper measured as CuO and from about 14.0 to about 50.0% by weight arsenic measured as $As_2O_5$; the improvement comprising having in said solution trivalent chromium in a ratio of hexavalent chromium to trivalent chromium of from about 4.0:1.0 to about 1.0:1.0 and a pH below about 2.0.

2. A wood treating solution as in claim 1 wherein the ratio of hexavalent chromium to trivalent chromium is from about 2.2:1.0 to about 1.5:1.0.

3. In a method for treating wood with a chromated copper arsenate solution comprising impregnating the wood with a 1 to 10 percent by weight solution of a chromated copper arsenate composition; the improvement comprising having in said solution trivalent chromium in a ratio of hexavalent chromium to trivalent chromium of from about 4.0:1.0 to about 1.0:1.0.

4. A method as in claim 3 wherein the ratio of hexavalent chromium to trivalent chromium is from about 2.2:1.9 to about 1.5:1.0.

* * * * *

UNITED STATES PATENT OFFICE
CERTIFICATE OF CORRECTION

PATENT NO. : 3,957,494
DATED : May 18, 1976
INVENTOR(S) : William J. Oberley

It is certified that error appears in the above-identified patent and that said Letters Patent are hereby corrected as shown below:

Claim 4 line 3 should appear as follows:

"2.2: 1.0 to about 1.5:1.0"

Signed and Sealed this

Twenty-second Day of March 1977

[SEAL]

Attest:

RUTH C. MASON
*Attesting Officer*

C. MARSHALL DANN
*Commissioner of Patents and Trademarks*